| United States Patent [19] | [11] 4,016,267 |
| Albrecht et al. | [45] Apr. 5, 1977 |

[54] SULFACYTOSINE DERIVATIVES

[75] Inventors: Harry Allen Albrecht, Towaco; John Thomas Plati, Rutherford, both of N.J.

[73] Assignee: Hoffmann-La Roche Inc., Nutley, N.J.

[22] Filed: June 7, 1976

[21] Appl. No.: 693,571

Related U.S. Application Data

[60] Continuation-in-part of Ser. No. 587,452, June 16, 1975, abandoned, which is a division of Ser. No. 480,784, June 19, 1974, Pat. No. 3,923,792.

[52] U.S. Cl. .............................. 424/229; 424/251
[51] Int. Cl.$^2$ ..................................... A61K 31/625
[58] Field of Search ............ 424/229, 251; 587/452

[56] References Cited

UNITED STATES PATENTS

| 3,375,247 | 3/1968 | Doub et al. ................... 260/239.75 |
| 3,422,098 | 1/1969 | Schmidt et al. .............. 260/239.75 |
| 3,457,278 | 7/1969 | Zimmermann ............... 260/239.75 |

*Primary Examiner*—Jerome D. Goldberg
*Attorney, Agent, or Firm*—Samuel L. Welt; George M. Gould; William G. Isgro

[57] ABSTRACT

$N^1$-(1,2-dihydro-2-oxo-4-pyrimidinyl)sulfanilamides, bearing a lower alkyl, cycloalkyl or cycloalkyl-lower alkyl substituent in the 1-position, prepared by reaction of the corresponding 1-substituted-1,2-dihydro-2-oxo-4-aminopyrimidine and N-acylated sulfanilyl chloride with subsequent hydrolysis, are described. The end products are useful as antibacterial agents.

11 Claims, No Drawings

SULFACYTOSINE DERIVATIVES

CROSS-REFERENCE TO RELATED APPLICATIONS

This application is a continuation-in-part of U.S. patent application Ser. No. 587,452, filed June 16, 1975, now abandoned, which in turn is a division of U.S. patent application Ser. No. 480,784, filed June 19, 1974, now U.S. Pat. No. 3,923,792, issued Dec. 2, 1975.

BRIEF SUMMARY OF THE INVENTION

The invention relates to compounds of the formula

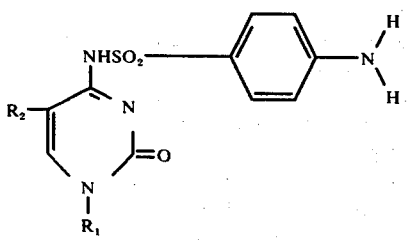

wherein $R_1$ is lower alkyl, cyclo-lower alkyl or cyclo-lower alkyl-lower alkyl; $R_2$ is hydrogen or lower alkyl; provided that when $R_1$ is lower alkyl, then $R_2$ must be lower alkyl;
and salts thereof with pharmaceutically acceptable bases. The compounds of formula I are useful as antibacterial agents.

DETAILED DESCRIPTION OF THE INVENTION

The invention relates to compounds of the formula

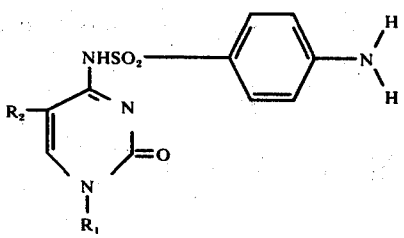

wherein $R_1$ is lower alkyl, cyclo-lower alkyl or cyclo-lower alkyl-lower alkyl; $R_2$ is hydrogen or lower alkyl; provided that when $R_1$ is lower alkyl, then $R_2$ must be lower alkyl;
and salts thereof with pharmaceutically acceptable bases.

As used herein, the term "lower alkyl" denotes a straight or branched chain saturated hydrocarbon of 1–7 carbon atoms, for example, methyl, ethyl, propyl, isopropyl, butyl, t-butyl, neopentyl, pentyl, heptyl, and the like; methyl is preferred. The term "cyclo-lower alkyl" denotes a cyclic hydrocarbon of 3–8 carbon atoms such as cyclopropyl, cyclobutyl, cyclopentyl, cyclohexyl, and the like. The term "cyclo-lower alkyl-lower alkyl" denotes a lower alkyl group as defined above wherein a hydrogen atom is substituted by a cyclo-lower alkyl group as defined above. The term "alkanoyl" denotes a group derived from an aliphatic carboxylic acid of 1–7 carbon atoms, for example, formyl, acetyl, propionyl, and the like.

The compounds of the invention are prepared by reacting a compound of the formula

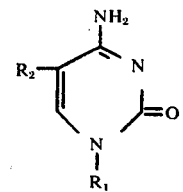

wherein $R_1$ and $R_2$ are as hereinbefore described, with a compound of the formula

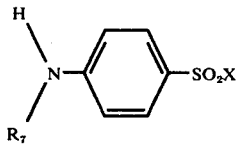

wherein $R_7$ is alkanoyl, and X is chlorine, bromine or iodine, preferably chlorine.

Compounds of formula I, wherein $R_2$ is hydrogen and $R_1$ is cyclo-lower alkyl or cyclo-lower alkyl-lower alkyl are a preferred group of compounds. Preferred compounds of formula I are:

$N^1$-(1-cyclopropylmethyl-1,2-dihydro-2-oxo-4-pyrimidinyl)-sulfanilamide;
$N^1$-(1-cyclopentyl-1,2-dihydro-2-oxo-4-pyrimidinyl)-sulfanilamide;
$N^1$-(1-cyclopropyl-1,2-dihydro-2-oxo-4-pyrimidinyl)-sulfanilamide;
$N^1$-(1-cyclohexyl-1,2-dihydro-2-oxo-4-pyrimidinyl)-sulfanilamide;
$N^1$-(1-cyclohexyl-1,2-dihydro-5-methyl-2-oxo-4-pyrimidinyl)-sulfanilamide;
$N^1$-(1-ethyl-1,2-dihydro-5-methyl-2-oxo-4-pyrimidinyl)-sulfanilamide;
$N^1$-(1-cyclopropyl-1,2-dihydro-5-methyl-2-oxo-4-pyrimidinyl)-sulfanilamide and the like.

A most preferred compound of formula I of the invention is $N^1$-(1-cyclopropyl-1,2-dihydro-2-oxo-4-pyrimidinyl)-sulfanilamide.

The compounds of formula I form pharmaceutically acceptable acid addition salts with bases. Such bases include alkali metal hydroxides such as sodium hydroxide, potassium hydroxide or the like; or amines such as dicyclohexylamine ethylamine, ethanolamine or the like.

The starting materials of formula II are prepared according to the procedures described in the Examples. Exemplary of the compounds of formula II are:

1-cyclopropylmethylcytosine (also known as 1-cyclopropylmethyl-1,2-dihydro-2-oxo-4-aminopyrimidine);
1-cyclopentylcytosine (also known as 1-cyclopentyl-1,2-dihydro-2-oxo-4-aminopyrimidine);
1-cyclopropylcytosine (also known as 1-cyclopropyl-1,2-dihydro-2-oxo-4-aminopyrimidine);
1-cyclohexylcytosine (also known as 1-cyclohexyl-1,2-dihydro-2-oxo-4-aminopyrimidine);

1-cyclohexyl-5-methylcytosine (also known as 1-cyclohexyl-1,2-dihydro-5-methyl-2-oxo-4-aminopyrimidine);

1-ethyl-5-methylcytosine (also known as 1-ethyl-1,2-dihydro-5-methyl-2-oxo-4-aminopyrimidine);

1-cyclopropyl-5-methylcytosine (also known as 1-cyclopropyl-1,2-dihydro-5-methyl-2-oxo-4-aminopyrimidine); or the like.

A cytosine of formula II is conveniently reacted with a sulfanilyl chloride, -bromide, or -iodide, preferably the -chloride of formula III in the presence of a base, for example, pyridine, or a trialkylamine such as triethylamine or trimethylamine, with or without an inert organic solvent such as acetonitrile or the like. The reaction temperature is not critical; preferably, the reaction is carried out at room temperature. The resulting product of formula I can be recovered utilizing conventional procedures, for instance, by crystallization or the like. The $N^4$-alkanoyl derivative of formula I, as described in the Examples, can be deacylated according to known procedures. For example, the alkanoyl derivative is treated with an alkali metal hydroxide such as sodium hydroxide. The deacylation is preferably carried out at an elevated temperature, for example, at a temperature in the range of from about 25° to 100° C. The reaction product, which is a compound of formula I, can be recovered utilizing conventional procedures, for example, crystallization or the like.

The compounds of formula III are known compounds or can be prepared in accordance with known procedures. Exemplary of such compounds are:

N-acetylsulfanilyl chloride;
N-acetylsulfanilyl bromide;
or the like.

The compounds of formula I and its pharmaceutically acceptable salts with bases are usesul as antibacterial agents, e.g., against S. aureus Smith, S. pyogenes 4, P. vulgaris 190 and S. typhosa P58a. The antibacterial activity of the claimed compounds can be demonstrated in warm-blooded animals, for exmaple, in Swiss albino mice weighing 18 to 20 gms. The mice are infected intraperitoneally with 0.5 ml. of an inoculum containing 100 to 1000 minimal lethal doses of the organism prepared in 5% hog gastric mucin, except for S. pyogenes 4 which is suspended papain digested bacto beef broth. The infecting inocule are prepared from overnight broth cultures. The test substance is administered orally as follows: two treatments, 5 hours apart, on the day of and day following infection, and one treatment on the second and third days following infection. Mice which die are autopsied and cultures are taken from heart blood, the survivors are observed for a period of 2 weeks.

For such use, the presently disclosed compounds are formulated, using conventional inert pharmaceutical adjuvant materials, into dosage forms which are suitable for oral or parenteral administration. Such dosage forms include tablets, suspensions, solutions, etc. Furthermore, the compounds of this invention can be embodied into, and administered in the form of, suitable hard or soft capsules. The identity of the inert adjuvant materials which are used in formulating the present compounds into oral and parenteral dosage forms will be immediately apparent to persons skilled in the art. These adjuvant materials, either inorganic or organic in nature, include, for example, water, gelatin, lactose, starch, magnesium stearate, talc, vegetable oils, gums, polyalkyleneglycols, etc. Moreover, preservatives, stabilizers, wetting agents, emulsifying agents, salts for altering osmotic pressure, buffers, etc. can be incorporated, if desired, into such formulations.

The quantity of active medicament which is present in any of the abovedescribed dosage forms is variable. It is preferred, however, to provide capsules or tablets containing from about 100 mg. to about 500 mg. of the formula I base or an equivalent amount of a medicinally acceptable base addition salt thereof.

The frequency with which any such dosage form will be administered to a patient or a host, i.e. a warm-blooded animal, will vary, depending upon the quantity of active medicament present therein and the needs and requirements of the patient, as diagnosed by the prescribing physician. Under ordinary circumstances, however, up to about 80 mg/kg. of the compound can be administered daily in several dosages. It is to be understood, however, that the dosages set forth therein are exemplary only and that they do not, to any extent, limit the scope or practice of this invention.

The sulfacytosine derivatives of the invention can also be used in combination with known potentiators of the 2,4-diamino-5-benzylpyrimiding type having the formula

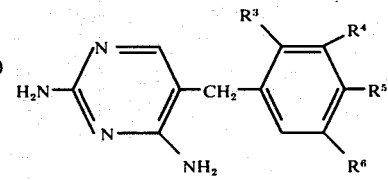

IV wherein $R^3$ is hydrogen or lower alkyl, $R^4$ is hydrogen or lower alkoxy, $R^5$ is amino, lower alkylamino, di-lower alkylamino or lower alkoxy, and $R^6$ is lower alkoxy, provided that when $R^3$ is lower alkyl, $R^4$ is hydrogen and $R^5$ is lower alkoxy, or pharmaceutically acceptable acid addition salts thereof.

The potentiators of formula IV above may be prepared by chlorinating or brominating a compound of the formula

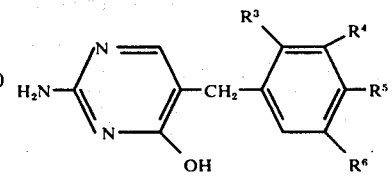

V wherein $R^3$, $R^4$, $R^5$ and $R^6$ are as defined in formula IV above, and treating the halo compound obtained with ammonia.

The reaction with ammonia is preferably carried out using a lower alkanol as solvent, preferably methanol. A suitable temperature range is from about 80° C. to about 200° C., preferably from about 100° C. to about 150° C. Since said temperature range is above the boiling point of methanol, the reaction is performed in a "closed system", e.g., in an autoclave. The chlorinating or brominating step as the case may be, is performed in the usual manner as known to all persons skilled in the art.

The potentiators of formula IV above may be transformed into pharmaceutically acceptable acid addition salts by contacting these compounds with suitable acids. Examples of suitable acids are hydrochloric acid, sulfuric acid, phosphoric acid, formic acid, acetic acid, malonic acid, succinic acid, maleic acid, citric acid, tartaric acid, malic acid, fumaric acid, methane sulfonic acid, or p-toluenesulfonic acid, etc.

Compositions comprising sulfacytosine derivatives and potentiators are prepared by mixing the components, whereby the sulfonamide and the potentiator may be present in a weight by weight ratio of from about 1:1 to about 40:1, preferably about 5:1. The mixing of the components may be performed in a known manner. These compositions are useful as antibacterial agents and are administered and used in the same manner as described hereinbefore for the compounds of formula I.

Preferred compounds of formula IV are:

2,4-diamino-5-(3,4,5-trimethoxybenzyl)-pyrimidine;
2,4-diamino-5(4-amino-3,5-dimethoxybenzyl)-pyrimidine; and
2,4-diamino-5-(2-methyl-4,5-dimethoxybenzyl)-pyrimidine.

The following Examples further illustrate the invention. All temperatures are in degrees Centigrade, unless otherwise mentioned.

EXAMPLE 1

Preparation of 3-cyclopropylmethylaminopropionitrile

With stirring and cooling in ice to maintain a reaction temperature of 8–10°, 16.4 g. of acrylonitrile was added to 22 g. of aminomethylcyclopropane. The mixture was allowed to warm to room temperature, with intermittent cooling for about 1 hour to maintain the temperature below 25°, and then allowed to stand overnight. The mixture was heated for 1 hour on a steam bath and then distilled under reduced pressure to obtain 32.0 g. of 3-cyclopropylmethylaminopropionitrile, boiling at 101°–102° at 7 mm.

EXAMPLE 2

Preparation of a mixture of 1-(2-cyanoethyl)-1-cyclopropylmethylurea and 1-cyclopropylmethyl-5,6-dihydrocytosine With cooling in ice to maintain the reaction at 25°–30°, 19.1 ml. of concentrated hydrochloric acid was added to 29.8 g. of 3-cyclopropylmethylaminopropionitrile to adjust the pH to 6.50. A total of 20.1 g. of 97% potassium cyanate was then added in four equal portions at 1 hour intervals. After the first portion was added, the reaction mixture was heated to 50° and maintained at 48°–50° with stirring overnight. The mixture was evaporated under reduced pressure with heating on a steam bath. The mixture was twice more evaporated to dryness after addition of 25 ml. portions of benzene. The residue was boiled for five minutes with 50 ml. of isopropanol, and the insoluble portion filtered off from the hot mixture and washed with an additional 10 ml. of hot isopropanol. The combined filtrate and wash was cooled in ice and allowed to crystallize for 2 hours before filtering the mixture of 1-(2-cyanoethyl)-1-cyclopropylmethylurea and 1-(cyclopropylmethyl-5,6-dihydrocytosine and washing with cold isopropanol; yield 28.9 g., m.p. 76°–100°. This product showed two spots, at $R_f$'s of 0.54 and 0.92 (1:1 methanol-chloroform on Silica gel) when visualized in an iodine chamber. The mixture was used directly for the preparation of 5-bromo-1-cyclopropylmethyl-5,6-dihydrocytosine.

EXAMPLE 3

Preparation of 1-(2-cyanoethyl)-1-cyclopropylmethylurea

This compound was isolated from the mixture of Example 2 by two recrystallizations from ethanol. This product, which corresponded to the spot at higher $R_f$'s on Tlc, melted at 84°–87°.

Analysis Calcd. for: $C_8H_{13}N_3O$: C, 57.47; H, 7.84; N, 25.13; Found: C, 57.44; H, 8.01; N, 25.18.

EXAMPLE 4

Preparation of 1-cyclopropylmethyl-5,6-dihydrocytosine 0.84 g. of the mixture of products obtained in Example 2 was refluxed for 45 minutes in 8 ml. of ethanol containing 0.10 g. of sodium methoxide. On cooling in ice, 0.50 g. of crystalline product separated, corresponding on Tlc to the spot of lower $R_f$. After recrystallization from ethanol, the obtained 1-cyclopropylmethyl-5,6-dihydrocytosine melted at 213°–214°.

Analysis Calcd. for $C_8H_{13}N_3O$: C, 57.47; H, 7.84; N, 25.13; Found: C, 57.28H, 7.89; N, 25.30.

EXAMPLE 5

Preparation of 5-bromo-1-cyclopropylmethyl-5,6-dihydrocytosine

To a solution of 8.10 g. of sodium methoxide in 150 ml. of methanol was added 25.0 g. of the mixture of 1-cyanoethyl-1-cyclopropylmethylurea and 1-cyclopropylmethyl-5,6-dihydrocytosine obtained in Example 2. The mixture was refluxed for 45 minutes, and then cooled in ice, whereupon crystallization occurred. With stirring and cooling to maintain the reaction at 3°–5°, 24.0 g. of bromine was added over a period of 20 minutes. The precipitate redissolved during this addition. The mixture was allowed to warm to room temperature and to stand for three days, during which time crystallization occurred. After chilling in ice, the resulting 5-bromo-1-cyclopropylmethyl-5,6-dihydrocytosine was filtered, washed with cold methanol, and dried in a vacuum desiccator over potassium hydroxide; yield 31.1 g., m.p. 139°–143° with resolidification. Recrystallization of 30.1 g. of product, from 21. of methanol, yielded 17.1 g. of 5-bromo-1-cyclopropylmethyl-5,6-dihydrocytosine melting at 143°–145° with resolidification.

Analysis Calcd. for $C_8H_{12}BrN_3O$: C, 39.04; H, 4.91; N, 17.07; Found: C, 38.91; H, 4.95; N, 17.03.

EXAMPLE 6

Preparation of 1-cyclopropylmethylcytosine

To a solution of 4.55 g. of 85% potassium hydroxide in 93 mml. of methanol cooled to 5°, was added 17.0 g. of 5-bromo-1-cyclopropylmethyl-5,6-dihydrocytosine. The mixture was stirred and allowed to warm spontaneously. When the initial reaction, which had warmed the mixture to 30°, subsided, the mixture was refluxed for 5 minutes and allowed to cool and stand at room temperature overnight. The suspension was evaporated under reduced pressure on a water bath at 86°. The residue was triturated was 300 ml. of water on a steam bath and chilled in ice before filtering. The resulting 1-cyclopropylmethylcytosine was washed with cold water and dried in a vacuum desiccator over potassium hydroxide; yield, 9.50 g., m.p. 264°–266°. A sample for analysis was recrystallized from ethanol; m.p. 265°–267°.

Analysis Calcd. for $C_8H_{11}N_3O$: C, 58.17; H, 6.71; N, 25.44; Found: C, 58.23; H, 6.39; N, 25.72.

EXAMPLE 7

Preparation of
$N^4$-Acetyl-$N^1$-(1-cyclopropylmethyl-1,2-dihydro-2-oxo-4-pyrimidinyl)sulfanilamide A. A mixture of 7.60 g. of 1-cyclopropylmethylcytosine, 10.8 g. of N-acetylsulfanilyl chloride and 30 ml. of pyridine was stirred overnight. The mixture was diluted slowly with 300 ml. of water and acidified by addition of 50 ml. of 6N hydrochloric acid. The mixture was allowed to stand for 5 hours to complete the crystallization, before filtering and washing with water; yield 13.5 g. of $N^4$-acetyl-$N^1$-(1-cyclopropylmethyl-1,2-dihydro-2-oxo-4-pyrimidinyl)sulfanilamide, m.p. 218°–223°.

B. A mixture of 495 mg. of 1-cyclopropylmethylcytosine, 702 mg. of N-acetylsulfanilyl chloride, 10 ml. of acetonitrile and 322 mg. of triethylamine was stirred and refluxed for 18 hours. The solvent was evaporated under reduced pressure, and the residue triturated with 10 ml. of water and 3 ml. of 10% aqueous sodium hydroxide. The alkaline solution was decanted from the dark insoluble portion and cleared by filtration. Addition of acetic acid to about pH 5 gave a gummy precipitate which solidified only very slowly. The aqueous solution was decanted and the gum triturated with 2 ml. of hot ethanol, and allowed to settle in an ice bath to obtain after filtration 280 mg. of product, melting at 222°–224°. A sample for analysis was recrystallized from aqueous ethanol; m.p. 225°–226°.

Analysis Calcd. for $C_{16}H_{18}N_4O_4S$: C, 53.03; H, 5.00; N, 15.46; Found: C, 52.94; H, 5.09; N, 15.32.

EXAMPLE 8

Preparation of
$N^1$-(1-cyclopropylmethyl-1,2-dihydro-2-oxo-4-pyrimidinyl)-sulfanilamide A mixture of 14.6 g. of $N^4$-acetyl-$N^1$-(1-cyclopropylmethyl-1,2-dihydro-2-oxo-4-pyrimidinyl)sulfanilamide and 146 ml. of 10% aqueous sodium hydroxide was heated on a steam bath for 1 hour after the temperature reached 85°. After dilution with 300 ml. of water, the mixture was filtered and acidified to about pH 5 by gradual addition of acetic acid. The initially gummy precipitate quickly solidified. The lumpy solid was crushed, filtered, washed with water, and dried in a vacuum desiccator over potassium hydroxide to yield 10.4 g. of $N^1$-(1-cyclopropylmethyl-1,2-dihydro-2-oxo-4-pyrimidinyl)sulfanilamide, m.p. 87°–95°. Recrystallization of 10.0 g. of this product from 60 ml. of 50% ethanol and drying in a vacuum desiccator over potassium hydroxide gave hydrated crystals which required further drying at 60° under reduced pressure, yield 8.03 g., m.p. 90°–92°.

Analysis Calcd. for $C_{14}H_{16}N_4O_3S$: C, 52.49; H, 5.03; N, 17.49; Found: C, 52.24; H, 5.18; N, 17.32.

EXAMPLE 9

Preparation of 3-cyclopentylaminopropionitrile

With stirring and cooling in an ice bath to control the temperature at 10°–15°, 36.4 g. of acrylonitrile was added to 58.4 g. of cyclopentylamine over a period of 20 minutes. The mixture was allowed to warm spontaneously to 30°, and then cooled intermittently for about 30 minutes, until the reaction subsided. After standing overnight, the mixture was heated for 1 hour on a steam bath and distilled under reduced pressure to yield 82.4 g. of 3-cyclopentylaminopropionitrile, b.p. 113°–115° at 9 mm.

EXAMPLE 10

Preparation of 1-(2-cyanoethyl)-1-cyclopentylurea

With stirring and cooling to maintain a reaction temperature of 25°–30°, 45.5 ml. concentrated hydrochloric acid was added to 76.0 g. of 3-cyclopentylaminopropionitrile to obtain a final pH of 6.50. A total of 46.0 g. of 97% potassium cyanate was then added in four equal portions at 1-hour intervals. After the first portion was added, the reaction was heated to 50° and maintained at 48°–50° with stirring overnight. The mixture was evaporated under reduced pressure with heating on a steam bath. The mixture was twice more evaporated to dryness after the addition of 80 ml. portions of benzene. The residue was triturated with 120 ml. of boiling isopropanol. The potassium chloride was removed by filtration and washed with 20 ml. of hot isopropanol, and the filtrate allowed to crystallize in an ice bath to yield 65 g. of 1-(2-cyanoethyl)-1-cyclopentylurea, m.p. 81°–84°.

EXAMPLE 11

Preparation of
5-bromo-1-cyclopentyl-5,6-dihydrocytosine

To a solution of 17.8 g. of sodium methoxide in 330 ml. of methanol was added 59.7 g. of 1-cyanoethyl-1-cyclopentylurea. The mixture was stirred and heated on a steam bath for 30 minutes and then cooled in ice. At 5°–8°, 52.9 g. of bromine was added over a period of 30 minutes. The ice bath was removed. Thereafter, the mixture was allowed to warm to room temperature and stand for 3 days, during which time crystallization occurred. The mixture was chilled in ice before filtering the product, which was washed with cold methanol and then with ether to yield 69.8 g. of 5-bromo-1-cyclopentyl-5,6-dihydrocytosine, m.p. 134°–144° with resolidification.

EXAMPLE 12

Preparation of 1-cyclopentylcytosine

To a solution of 15.8 g. of 85% KOH in 320 ml. of methanol was added at 10°, 62.4 g. of 5-bromo-1-cyclopentyl-5,6-dihydrocytosine. The mixture was stirred and allowed to warm spontaneously to a maximum temperature of 31° after 15 minutes. When the initial reaction subsided, the mixture was refluxed on a steam bath for five minutes. After standing overnight at room temperature, the mixture was evaporated to dryness under reduced pressure. The residue was dissolved in 100 ml. of water by heating quickly to 80° on a steam bath, and the solution filtered through a sintered glass funnel before cooling in ice to 30°. The product was allowed to crystallize at room temperature for 2 hours before filtering to yield 38.8 g. of 1-cyclopentylcytosine, m.p. 183°–198°. The product was used directly in the subsequent reaction with N-acetylsulfanilyl chloride.

A sample for analysis was prepared by purification via the hydrochloride, as follows: The 1-cyclopentylcytosine (10.0 g.) was dissolved in 40 ml. of warm ethanol, and the mixture strongly acidified by addition of ethanolic HCl. The hot solution was cleared by filtration and allowed to crystallize at room temperature to yield 6.07 g. of 1-cyclopentylcytosine hydrochloride, m.p. 204°–209°. A solution of 5.30 g. of the hydrochloride in 10 ml. of hot water was made strongly alkaline by addition of excess 10% aqueous sodium hydroxide solution, which was allowed to crystallize at room temperature to yield 3.75 g. of 1-cyclopentylcytosine, m.p. 229°–233°.

Analysis Calcd. for $C_9H_{13}N_3O$: C, 60.32; H, 7.31; N, 23.45; Found: C, 60.19; H, 7.57; N, 23.64.

EXAMPLE 13

Preparation of
$N^4$-Acetyl-$N^1$-(1-cyclopentyl-1,2-dihydro-2-oxo-4-pyrimidinyl)-sulfanilamide A mixture of 240 g. of 1-cyclopentylcytosine, 31.4 g. of N-acetylsulfanilyl chloride and 80 ml. of pyridine was stirred after controlling the initial reaction by momentary cooling to keep the reaction temperature below 35°. The mixture was diluted with 800 ml. of water and acidified to pH 1–2 by the addition of 148 ml. of 6N hydrochloric acid. After 4 hours, the supernatant liquid was decanted from the viscous gummy precipitate. The gum was dissolved in 100 ml. of warm ethanol and 100 ml. of water was added. The mixture was stirred for 3 hours as crystallization occurred to yield 26.3 g. of $N^4$-acetyl-$N^1$-(1-cyclopentyl-1,2-dihydro-2-oxo-4-pyrimidinyl)sulfanilamide, m.p. 219°–228°. The decantate from the initially viscous gummy precipitate also deposited crystals of $N^4$-acetyl-$N^1$-(1-cyclopentyl-1,2-dihydro-2-oxo-4-pyrimidinyl)-sulfanilamide during 3 hours; additional yield 2.80 g., m.p. 230°–234°.

EXAMPLE 14

Preparation of
$N^1$-(1-cyclopentyl-1,2-dihydro-2-oxo-4-pyrimidinyl)-sulfanilamide A mixture of 29.1 g. of $N^4$-acetyl-$N^1$-(1-cyclopentyl-1,2-dihydro-2-oxo-4-pyrimidinyl)sulfanilamide and 290 ml. of 10% aqueous sodium hydroxide was heated on a steam bath for 1 hour, diluted with 290 ml. of tap water, and acidified by addition of 60 ml. of acetic acid. The initially oily precipitate solidified over a period of several hours to yield 21.1 g. of product melting over a wide range. The resulting product was dissolved in 200 ml. of boiling methanol. treated with charcoal, and the filtered solution evaporated under reduced pressure to a volume of 65 ml., which crystallized at room temperature to yield 15.2 g. of $N^1$-(1-cyclopentyl-1,2-dihydro-2-oxo-4-pyrimidinyl)sulfanilamide, m.p. 167°–171°. The product was dissolved in 150 ml. of methanol. The volume was reduced to 60 ml. by evaporation under reduced pressure, and the product allowed to crystallize at room temperature to yield 12.7 g. of $N^1$-(1-cyclopentyl-1,2-dihydro-2-oxo-4-pyrimidinyl)sulfanilamide, m.p. 168°–171°.

Analysis Calcd. for $C_{15}H_{18}N_4O_3S$: C, 53.88; H, 5.43; N, 16.76; Found: C, 53.78; H, 5.23; N, 16.62.

EXAMPLE 15

Preparation of 3-cyclopropylaminopropionitrile

With stirring and cooling to maintain a reaction temperature of 10°–15°, 46.5 g. of acrylonitrile was added to 50.0 g. of cyclopropylamine. When the addition was complete, the reaction mixture was allowed to warm spontaneously to a maximum temperature of 30°, and then allowed to stand overnight at room temperature. After heating 1 hour on a steam bath and distillation under reduced pressure, 64.8 g. of 3-cyclopropylaminopropionitrile, b.p. 90°–92° at 12 mm., was obtained.

EXAMPLE 16

Preparation of 1-(2-cyanoethyl)-1-cyclopropylurea

With stirring and cooling in ice, 46 ml. of concentrated hydrochloric acid was added to 64.8 g. of 3-cyclopropylaminopropionitrile at 25°–30° to obtain a final pH of 6.00. A total of 49.3 g. of 97% potassium cyanate was then added in four portions at intervals of 1 hour. After the first portion was added, the mixture was warmed to 50° and maintained at 45°–50° with stirring overnight. The mixture was evaporated to dryness under reduced pressure with warming on a steam bath. After the addition of 100 ml. of benzene, the mixture was again evaporated to dryness. The residue was extracted by trituration with a total of 600 ml. of boiling isopropanol in two portions, and the filtered solution allowed to crystallize in an ice bath to yield 55.3 g. of 1-(2-cyanoethyl)-1-cyclopropylurea, m.p. 119°–123°.

EXAMPLE 17

Preparation of
5-bromo-1-cyclopropyl-5,6-dihydrocytosine

To a solution of 17.8 g. of sodium methoxide in 330 ml. of methanol was added 50.5 g. of 1-(2-cyanoethyl)-1-cyclopropylurea. The mixture was refluxed for 30 minutes, and cooled in ice. With stirring at 4°–6°, 52.9 g. of bromine was added over a period of 30 minutes. The mixture, containing some precipitate, was stirred overnight. After approximately 24 hours, a mild exothermic reaction was noted. As the original precipitate suddenly dissolved, a precipitate of white crystals began to separate. The mixture was allowed to stand for three days before filtering, whereby 55.9 g. of 5-bromo-2-cyclopropyl-5,6-dihydrocytosine, m.p. 135°–140° with resolidification, was obtained.

EXAMPLE 18

Preparation of 1-cyclopropylcytosine

To a solution of 15.2 g. of 85% potassium hydroxide in 310 ml. of methanol was added 53.3 g. of 5-bromo-1-cyclopropyl-5,6-dihydrocytosine. The mixture was allowed to warm spontaneously for 30 minutes and then refluxed with stirring for 5 minutes. The mixture was stirred for 1.5 hours, allowed to stand overnight, and evaporated under reduced pressure. The residue was dissolved in 80 ml. of water at 80°, and the solution after filtration was allowed to crystallize overnight in a refrigerator. The crystallized material was washed with ice-cold water and then with ether to yield 20.4 g. of 1-cyclopropylcytosine, m.p. 209°–223°.

EXAMPLE 19

Preparation of
N$^4$-Acetyl-N$^1$-(1-cyclopropyl-1,2-dihydro-2-oxo-4-pyrimidinyl)-sulfanilamide A mixture of 10.6 g. of 1-cyclopropylcytosine, 16.4 g. of N-acetylsulfanilyl chloride and 47 ml. of pyridine was stirred overnight after momentary cooling to maintain the reaction below 30°. The mixture was poured into 700 ml. of water, and after filtration by gravity, the solution was strongly acidified by addition of 6N hydrochloric acid. Gradual crystallization occurred overnight in a refrigerator before filtering the N$^4$-acetyl-N$^1$-(1-cyclopropyl-1,2-dihydro-2-oxo-4-pyrimidinyl)-sulfanilamide; yield 10.7 g., m.p. 139°–143°.

EXAMPLE 20

Preparation of
N$^1$-(1-cyclopropyl-1,2-dihydro-2-oxo-4-pyrimidinyl)-sulfanilamide A solution of 10.7 g. of N$^4$-acetyl-N$^1$-(1-cyclopropyl-1,2-dihydro-2-oxo-4-pyrimidinyl)sulfanilamide in 107 ml. of 10% aqueous sodium hydroxide was heated on a steam bath for 1 hour. After cooling below 35°, 15 ml. of acetic acid was added to precipitate a gum, which quickly solidified; yield 7.45 g., m.p. 119°–123°. Of this period, 7.35 g. was dissolved in 735 ml. of hot water by adding 12 ml. of 10% aqueous sodium hydroxide to obtain a strongly alkaline solution. After the addition of 5 ml. of acetic acid, the hot solution was immediately filtered and allowed to crystallize at room temperature to yield 5.95 g. of N$^1$-(1-cyclopropyl-1,2-dihydro-2-oxo-4-pyrimidinyl)sulfanilamide, m.p. 124°–126°.

The sample for analysis, after recrystallization from 80% ethanol, was found to contain water of crystallization.

Analysis Calcd. for $C_{13}H_{14}N_4O_3S \cdot H_2O$: C, 48.15; H, 4.97; N, 17.28; $H_2O$; 5.55; Found: C, 48.01; H, 4.81; N, 17.19; $H_2O$; 5.96.

EXAMPLE 21

Preparation of 3-cyclohexylaminopropionitrile

With stirring and intermittent cooling to maintain the reaction at 20°–25°, 53.0 g. of acrylonitrile was added over a 30-minute period to 99.0 g. of cyclohexylamine. Intermittent cooling was continued for another hour until the reaction subsided, and the mixture was allowed to stand overnight before distillation under reduced pressure to yield 109 g. of 3-cyclohexylaminopropionitrile, b.p. 75°–78° at 0.1 mm.

EXAMPLE 22

Preparation of 1-(2-cyanoethyl)-1-cyclohexylurea

With stirring and cooling in ice to maintain the reaction temperature below 35°, 57.8 ml. of concentrated hydrochloric acid and 40 ml. of water were added to 106.6 g. of 3-cyclohexylaminopropionitrile, followed by about 3 ml. of 10% aqueous sodium hydroxide to bring the final pH to 6.00. A total of 58.5 g. of 97% potassium cyanate was then added in four equal portions at one-hour intervals. After the first addition, the mixture was warmed to 50° and maintained at 45°–50° during the remainder of the reaction time. An additional 75 ml. of water was added when a thick precipitate separated, and stirring was continued overnight. The mixture was heated to 80° after adding 200 ml. of water, and then cooled to room temperature and filtered to yield 121 g. of 1-(2-cyanoethyl)-1-cyclohexylurea, m.p. 110°–112°.

EXAMPLE 23

Preparation of
5-bromo-1-cyclohexyl-5,6-dihydrocytosine

To a stirred solution of 27.0 g. of sodium methoxide in 500 ml. of methanol was added 97.5 g. of 1-(2-cyanoethyl)-1-cyclohexylurea. The mixture was refluxed for 30 minutes, cooled to 5°, and 80 g. of bromine was added at 5°–10° over a period of 30 minutes. The mixture was stirred at ambient temperature overnight, and the precipitate filtered and washed with methanol to yield 118.4 g. of 5-bromo-1-cyclohexyl-5,6-dihydrocytosine, m.p. 152°–156° with resolidification.

EXAMPLE 24

Preparation of 1-cyclohexylcytosine

To a stirred solution of 27.7 g. of 85% potassium hydroxide in 570 ml. of methanol at 10° was added 115 g. of 5-bromo-1-cyclohexyl-5,6-dihydrocytosine. The mixture was allowed to warm spontaneously, reaching a maximum temperature of 33° after 13 minutes. After about 1 hour, the mixture was refluxed for 5 minutes and allowed to cool to room temperature with continued stirring for 2 hours. After standing overnight, the mixture was evaporated under reduced pressure. The residue was triturated with 500 ml. of water at 75° for 5 minutes and allowed to settle for 2 hours with cooling in ice to yield 70.7 g. of a product, m.p. 213°–231°. Of this product, 65.0 g. was recrystallized from 375 ml. of methanol to yield 42.7 g. of 1-cyclohexylcytosine, m.p. 252°–258°.

EXAMPLE 25

Preparation of
N$^4$-Acetyl-N$^1$-(1-cyclohexyl-1,2-dihydro-2-oxo-4-pyrimidinyl) sulfanilamide A mixture of 29.0 g. of 1-cyclohexylcytosine, 90 ml. of pyridine and 35.1 g. of N-acetylsulfanilyl chloride was stirred overnight, poured into 900 ml. of water, and acidified by addition of 80 ml. of concentrated hydrochloric acid. After several hours of vigorous stirring, the precipitated product solidified to yield 33.3 g. of N$^4$-acetyl-N$^1$-(1-cyclohexyl-1,2-dihydro-2-oxo-4-pyrimidinyl-sulfanilamide, m.p. 219°–234°. A sample purified by two recrystallizations from ethanol melted at 247°–250°.

EXAMPLE 26

Preparation of
N$^1$-(1-cyclohexyl-1,2-dihydro-2-oxo-4-pyrimidinyl)sulfanilamide A mixture of 27.9 g. of N$^4$-acetyl-N$^1$-(1-cyclohexyl-1,2-dihydro-2-oxo-4-pyrimidinyl)sulfanilamide and 280 ml. of 10% aqueous sodium hydroxide was stirred and heated on a steam bath for 1 hour, diluted with 280 ml. of water, cooled to room temperature, and acidified by dropwise addition of 56 ml. of acetic acid to precipitate a finely divided solid to yield 21.4 g. of crude N$^1$-(1-cyclohexyl-1,2-dihydro-2-oxo-4-pyrimidinyl)sulfanilamide, m.p. 100°–120°.

Dicyclohexylamine Salt

Of the product, 20.0 g. was dissolved in 120 ml. of hot ethanol and 11.5 g. of dicyclohexylamine was added. The hot solution was filtered quickly and then crystallization was allowed to proceed first at room temperature and then in a refrigerator overnight to yield 15.8 g. of the dicyclohexylamine salt of $N^1$-(1-cyclohexyl-1,2-dihydro-2-oxo-4-pyrimidinyl)sulfanilamide, m.p. 126°–128°. A sample for analysis was recrystallized from ethanol; it contained ethanol of crystallization.

Analysis Calcd. for $C_{30}H_{29}N_5O_4S$ ($C_{16}H_{20}N_4O_3S \cdot C_{12}H_{23}N \cdot C_2H_6O$) C, 62.58; H, 8.58; N, 12.16; Found: C, 62.34; H, 8.54; N, 12.23.

Of the above dicyclohexylamine salt, 15.5 g. was stirred with 300 ml. of water, 75 ml. of 10% aqueous sodium hydroxide and 250 ml. of ether. The ether was separated, and the aqueous phase washed again with 250 ml. of ether. The aqueous solution was diluted and 1200 ml. of water, heated to 90°, quickly acidified with 15 ml. of acetic acid, and allowed to stand three days before filtering the precipitate to yield 8.50 g. of $N^1$-(1-cyclohexyl-1,2-dihydro-2-oxo-4-pyrimidinyl)sulfanilamide, m.p. 153°–156°. This product was dissolved in 60 ml. of hot methanol, and the solution filtered and boiled down to a volume of 25 ml. before allowing to stand and crystallize overnight to yield 7.10 g. of $N^1$-(1-cyclohexyl-1,2-dihydro-2-oxo-4-pyrimidinyl)sulfanilamide, m.p. 155°–157°.

Analysis Calcd. for $C_{16}H_{20}N_4O_3S$: C, 55.16; H, 5.79; N, 16.08; Found: C, 54.94; H, 5.82; N, 16.36.

EXAMPLE 27

Preparation of 1-cyclohexyl-4-thiothymine

A solution of 8.20 g. of 1-cyclohexythymine[1] and 9.60 g. of phosphorous pentasulfide in 500 ml. of pyridine was refluxed for 9 hours, and the solvent distilled off under reduced pressure. The residue was triturated with 120 ml. of water to obtain a solid, which was dried in the air and recrystallized from 120 ml. of ethanol to yield 7.15 g. of 1-cyclohexyl-4-thiothymine, melting at 176°–179°.

[1]T. Okano, S. Goya and T. Takahashi, J. Pharm. Soc. Japan, 88, 1112 (1968).

A 300 mg. sample of product prepared as above was recrystallized from 6 ml. of ethanol to obtain 224 mg. of analytically pure 1-cyclohexyl-4-thiothymine, melting at 177°–178°.

EXAMPLE 28

Preparation of 1-cyclohexyl-5-methylcytosine 5.0 g. of 1-cyclohexyl-4-thiothymine was added to 120 ml. of ethanol which had been saturated with ammonia at 5°. The solution was heated under pressure at 120° for 22 hours. After removal from the pressure reactor, the mixture was reheated, filtered and concentrated by evaporation under reduced pressure to a volume of 60 ml. The solution was chilled in ice to obtain 3.28 g. of crystalline product. On further concentration, the mother liquor yielded a second crop of 0.69 g. The combined crops, which contained ethanol of crystallization, were distilled with 100 ml. of toluene until approximately 50 ml. of distillate was collected. The residue was chilled in ice to obtain 2.65 g. of 1-cyclohexyl-5-methylcytosine, melting at 205°–207°.

EXAMPLE 29

Preparation of $N^4$-acetyl-$N^1$-(1-cyclohexyl-1,2-dihydro-5-methyl-2-oxo-4-pyrimidinyl)sulfanilamide A mixture of 2.07 g. of 1-cyclohexyl-5-methylcytosine, 10 ml. of pyridine and 2.34 g. of N-acetylsulfanilyl chloride was stirred overnight, poured into 100 ml. of cold water, and acidified by addition of 18 ml. of 6N hydrochloric acid. Supernatant liquid was decanted from the gummy precipitate, which was washed with water, by decantation. The gum solidified on trituration with 10 ml. of ethanol to yield 1.75 g. of $N^4$-acetyl-$N^1$-(1-cyclohexyl-1,2-dihydro-5-methyl-2-oxo-4-pyrimidinyl)sulfanilamide, melting at 254°–256°. The product may be crystallized from ethanol.

EXAMPLE 30

Preparation of $N^1$-(1-cyclohexyl-1,2-dihydro-5-methyl-2-oxo-4-pyrimidinyl) sulfanilamide A mixture of 169 mg. of $N^4$-acetyl-$N^1$-(1-cyclohexyl-1,2-dihydro-5-methyl-2-oxo-4-pyrimidinyl)sulfanilamide and 1.7 ml. of 10% aqueous sodium hydroxide was heated on the steam bath for 30 minutes, diluted with an equal volume of water, and heated for another 30 minutes. The mixture was cooled and acidified by dropwise addition of acetic acid, diluted with 1 ml. of water and allowed to stand for 30 minutes before filtering. Of the crude product obtained (123 mg.), 94 mg. was dissolved in 2 ml. of warm methanol, and crystallized by evaporating to one-quarter volume in a stream of nitrogen, to obtain 48.9 mg. of $N^1$-(1-cyclohexyl-1,2-dihydro-5-methyl-2-oxo-4-pyrimidinyl)sulfanilamide, melting point 203°–206°.

EXAMPLE 31

Preparation of 1-ethyl-4-thiothymine

A mixture of 4.62 g. of 1-ethylthymine[2], 7.33 g. of phosphorus pentasulfide and 100 ml. of pyridine was refluxed for 8.5 hours. The pyridine was distilled off under reduced pressure, and the residue triturated with 50 ml. of water to obtain a solid, which was filtered and washed with four 10 ml. portions of water. After drying in the air, this material was crystallized from 100 ml. of ethanol to obtain 4.00 g. of 1-ethyl-4-thiothymine, melting at 204°–207°.

[2]K. Yamauchi and M. Kinoshita, J. Chem. Soc. Perkin I, 1973, 391.

A 300 mg. sample was recrystallized from 10 ml. of ethanol to obtain 219 mg. of 1-ethyl-4-thiothymine, melting at 205°–206°, for analysis.

EXAMPLE 32

Preparation of 1-ethyl-5-methylcytosine 3.40 g. of 1-ethyl-4-thiothymine was added to 100 ml. of ethanol which had been saturated with ammonia at 5°. The solution was heated under pressure at 120° for 24 hours. The mixture was cooled in ice, and the crystalline product filtered and washed with cold ethanol to obtain 2.00 g. of 1-ethyl-5-methylcytosine, melting at 244°–247°.

The melting point was unchanged when a sample for analysis was prepared by recrystallization from ethanol.

EXAMPLE 33

Preparation of N$^4$-acetyl-N$^1$-(1-ethyl-1,2-dihydro-5-methyl-2-oxo-4-pyrimidinyl) sulfanilamide A mixture of 1.53 g. of 1-ethyl-5-methylcytosine, 2.34 g. of N-acetylsulfanilyl chloride and 10 ml. of pyridine was stirred overnight, diluted with 100 ml. of cold water, filtered with a little Hyflo to remove turbidity and acidified by addition of 19 ml. of 6N hydrochloric acid. The product was allowed to crystallize for several hours at room temperature before filtering, washing with water, and drying in a vacuum desiccator over potassium hydroxide to obtain 1.78 g. of N$^4$-acetyl-N$^1$-(1-ethyl-1,2-dihydro-5-methyl-4-pyrimidinyl)-sulfanilamide, melting at 235°–239°.

EXAMPLE 34

Preparation of N$^1$-(1-ethyl-1,2-dihydro-5-methyl-2-oxo-4-pyrimidinyl) sulfanilamide A mixture of 1.00 g. of N$^4$-acetyl-N$^1$-(1-ethyl-1,2-dihydro-5-methyl-2-oxo-4-pyrimidinyl)sulfanilamide and 10 ml. of 10% aqueous sodium hydroxide was heated for 1 hour on the steam bath, diluted with 20 ml. of water, cooled and acidified by gradual addition of acetic acid. The solid precipitate was filtered and washed with water to obtain 0.72 g. of product melting at 174°–176°. Recrystallization of 0.50 g. of this product from 30 ml. of ethanol gave 0.35 g. of N$^1$-(1-ethyl-1,2-dihydro-5-methyl-2-oxo-4-pyrimidinyl)sulfanilamide, melting at 176°–178°.

EXAMPLE 35

Preparation of 1-cyclopropyl-4-thiothymine 10.24 g. of ethyl (2-methyl-3-piperidino-thioacryloyl)-carbamate[3] were added with stirring to a solution of 2.52 g. of cyclopropylamine in 40 ml. of ethanol. The mixture was cooled slightly to keep the temperature below 32° when the product rapidly crystallized. After 30 minutes, the mixture was chilled in ice and filtered, to obtain 5.45 g. of 1-cyclopropyl-4-thiothymine, melting at 178°–180°.

[3]R. W. Lamon, J. Het. Chem., 5, 837 (1968).

A sample for analysis was obtained by recrystallization from ethanol. The melting point was unchanged.

EXAMPLE 36

Preparation of 1-cyclopropyl-5-methylcytosine 7.50 g. of 1-cyclopropyl-4-thiothymine was added to 120 ml. of ethanol which had been saturated with ammonia at 5°. The solution was heated under pressure at 120° for 22 hours. The mixture was cooled in ice and the crystals filtered and washed with cold ethanol to obtain 5.33 g. of 1-cyclopropyl-5-methylcytosine, melting at 252°–256°.

A sample obtained for analysis by recrystallization from ethanol melted at 253°–255°.

EXAMPLE 37

Preparation of N$^4$-acetyl-N$^1$-(1-cyclopropyl-1,2-dihydro-5-methyl-2-oxo-4-pyrimidinyl)sulfanilamide A mixture of 0.83 g. of 1-cyclopropyl-5-methylcytosine, 1.17 g. of N-acetylsulfanilyl chloride and 4 ml. of pyridine was stirred overnight, diluted with 70 ml. of water, acidified with 8 ml. of 6N hydrochloric acid, and allowed to stand overnight in the refrigerator while gradual crystallization occurred. Filtration gave 0.60 g. of N$^4$-acetyl-N$^1$-(1-cyclopropyl-1,2-dihydro-5-methyl-2-oxo-4-pyrimidinyl)sulfanilamide, melting at 176°–181°.

EXAMPLE 38

Preparation of N$^1$-(cyclopropyl-1,2-dihydro-5-methyl-2-oxo-4-pyrimidinyl) sulfanilamide A mixture of 500 mg. of N$^4$-acetyl-N$^1$-(1-cyclopropyl-1,2-dihydro-5-methyl-2-oxo-4-pyrimidinyl)sulfanilamide and 5 ml. of 10% aqueous sodium hydroxide was heated on the steam bath for 1 hour, diluted with 10 ml. of water, cooled and acidified by gradual addition of 1ml. of acetic acid. The initial oily precipitate quickly solidified and filtration gave 332 mg. of product melting at 128°–133°. Recrystallization from 7 ml. of ethanol gave 120 mg. of N$^1$-cyclopropyl-1,2-dihydro-5-methyl-2-oxo-4-pyrimidinyl)sulfanilamide, melting at 134°–136°.

Example 39

| Capsule Formulation | Per Capsule |
|---|---|
| N.$^1$-(1-cyclohexyl-1,2-dihydro-2-oxo-4-pyrimidinyl)sulfanilamide | 50 mg. |
| Lactose, U.S.P. | 125 mg. |
| Corn Starch, U.S.P. | 30 mg. |
| Talc, U.S.P. | 5 mg. |
| Total | 210 mg. |

Procedure:

N$^1$-(1-cyclohexyl-1,2-dihydro-2-oxo-4-pyrimidinyl)-sulfanilamide is mixed with lactose and corn starch in a suitable mixer. The mixture is further blended by passing through a Fitzpatrick Comminuting Machine with a No. 1A screen with knives forward. The blended powder is returned to the mixer, the talc is added and blended thoroughly. The mixture is filled into No. 4 hard shell gelatin capsules on a Parke Davis capsulating machine.

EXAMPLE 40

| Tablet Formulation | Per Tablet |
|---|---|
| N$^1$-(1-cyclohexyl-1,2-dihydro-2-oxo-4-pyrimidinyl)sulfanilamide (2% excess) | 255 mg. |
| Dicalcium Phosphate Dihydrate, Unmilled | 230 mg. |
| Corn Starch | 70 mg. |
| FD&C Yellow No. 5 - Aluminum Lake 25% | 2 mg. |
| Durkee 117* | 25 mg. |
| Calcium Stearate | 3 mg. |
| Total Weight | 585 mg. |

*Mixture of di- and tri- C$_{16}$-C$_{18}$ fatty acid esters of glycerin (primarily stearic acid with smaller amounts of palmitic and oleic acids).

Procedure:

All the ingredients are mixed thoroughly and Fitzed (Model D) using a No. 1A screen, medium speed. The mixture is remixed and slugged. The slugs are screened on an Oscillator through a No. 14 mesh screen and compressed on an "E" machine.

EXAMPLE 41

| Tablet Formulation | mg/tab. |
| --- | --- |
| N¹-(1-cyclohexyl-1,2-dihydro-2-oxo-4 pyrimidinyl)sulfanilamide | 400 |
| 2,4-diamino-5-(3,4,5-trimethoxybenzyl)-pyrimidine | 80 |
| Microcrystalline Cellulose PH 102 | 75 |
| Corn Starch, Dried | 10 |
| Methylcellulose 400 cps | 9 |
| Microcrystalline Cellulose PH 1102 | 75 |
| Corn Starch, Dried | 40 |
| Magnesium Stearate | 2 |
| Total Tablet Weight | 691 |

Procedure:

N¹-(1-cyclohexyl-1,2-dihydro-2-oxo-4-pyrimidinyl)-sulfanilamide and 2,4-diamino-5-(3,4,5-trimethoxybenzyl)pyrimidines are mixed together in a suitable blender. The mixture is milled through a Fitzmill using No. 1 plate, hammers forward, high speed. The resulting mixture is granulated with 5% methylcellulose solution is distilled water and aged overnight in a refrigerator. The wet granulation is passed through a No. 5 screen, hammers forward, low speed, and dried overnight in a suitable oven at 120° F. The dried granulation is then milled through No. 2a plate, hammers forward, low speed. The microcrystalline cellulose PH 1102 and the dried corn starch are milled through a No. 1 screen, hammers forward, medium speed. The materials from the last two steps are mixed for 10 minutes in a suitable blender. The magnesium stearate is added to the above mixture and mixed for 2 minutes. The resulting material is then compressed into tablets having a weight of 691 mg. per tablet.

EXAMPLE 42

| Tablet Formulation | mg/tablet |
| --- | --- |
| N¹-(1-cyclohexyl-1,2-dihydro-2-oxo-4-pyrimidinyl)sulfanilamide | 800 |
| 2,4-diamino-5-(3,4,5-trimethoxybenzyl)-pyrimidine | 160 |
| Pregelatinized starch | 50 |
| Primojel | 50 |
| Magnesium Stearate | 5 |
| Total weight | 1065 mg. |

Procedure:

The N¹-(1-cyclohexyl-1,2-dihydro-2-oxo-4-pyrimidinyl)sulfanilamide and 2,4-diamino-5-(3,4,5-trimethoxybenzyl)pyrimidine are mixed together in a suitable mixer for 10 minutes. The resulting mixture is milled through a No. 1A plate, knives forward, medium speed, Fitzmill. The mixture from the foregoing step is granulated with distilled water. The resulting granulation is passed through a No. 5 screen, knives forward, slow speed, Fitzmill. The granulation is racked and oven dried at 120° F overnight. The dried granulation is passed through a No. 12 wire mesh screen on a Fitzmill at low speed, knives forward. Thereafter, the primojel and magnesium stearate are added, and the resulting mixture mixed for 5 minutes. The granulation is pressed at 1,065 mg. on a suitable rotary tablet press.

We claim:

1. An antibacterial composition comprising as the active ingredient an antibacterially effective amount of a compound of the formula

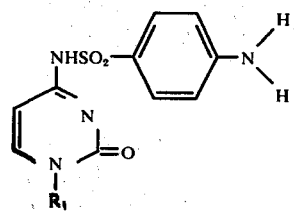

wherein $R_1$ is cyclo-lower alkyl or cyclo-lower alkyl-lower alkyl;

or a pharmaceutically acceptable salt thereof and an inert carrier material.

2. The antibacterial composition of claim 1 wherein $R_1$ is cyclo-lower alkyl-lower alkyl.

3. The antibacterial composition of claim 2 wherein the active ingredient is N¹-(1-cyclopropyl-methyl-1,2-dihydro-2-oxo-4-pyrimidinyl)-sulfanilamide.

4. The antibacterial composition of claim 1 wherein the active ingredient is N¹-(1-cyclopentyl-1,2-dihydro-2-oxo-4-pyrimidinyl)-sulfanilamide.

5. The antibacterial composition of claim 1 wherein the active ingredient is N¹-(1-cyclopropyl-1,2-dihydro-2-oxo-4-pyrimidinyl)-sulfanilamide.

6. The antibacterial composition of claim 1 wherein the active ingredient is N¹-(1-cyclohexyl-1,2-dihydro-2-oxo-4-pyrimidinyl)-sulfanilamide.

7. A method for combatting bacteria comprising administering to a warmblooded animal requiring such treatment an antibacterially effective amount of a compound of the formula

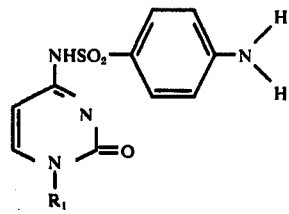

wherein $R_1$ is cyclo-lower alkyl or cyclo-lower alkyl-lower alkyl;

or a pharmaceutically acceptable salt thereof.

8. An antibacterial composition comprising an antibacterially effective combination of 1 to 40 parts of a sulfanilamide of the formula

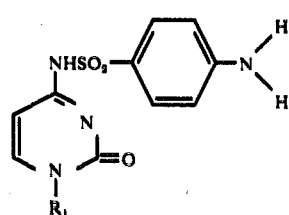

wherein $R_1$ is cyclo-lower alkyl or cyclo-lower alkyl-lower alkyl;

or a pharmaceutically acceptable salt thereof, and 1 part of a pyrimidine of the formula

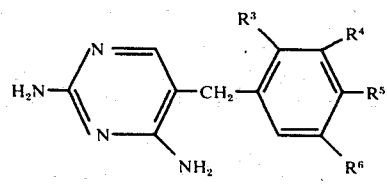

wherein $R^3$ is hydrogen or lower alkyl, $R^4$ is hydrogen or lower alkoxy, $R^5$ is amino, lower alkylamino, di-lower alkylamino or lower alkoxy, and $R^6$ is lower alkoxy, provided that when $R^3$ is lower alkyl, $R^4$ is hydrogen and $R^5$ is lower alkoxy, or pharmaceutically acceptable acid addition salt thereof and an inert carrier material.

9. The composition of claim 8 wherein the sulfanilamide is $N^1$-(1-cyclohexyl-1,2-dihydro-2-oxo-4-pyrimidinyl)-sulfanilamide and wherein the pyrimidine is 2,4-diamino-5-(3,4,5-trimethoxybenzyl)-pyrimidine.

10. The composition of claim 8 wherein the sulfanilamide is $N^1$-(1-cyclohexyl-1,2-dihydro-2-oxo-4-pyrimidinyl)-sulfanilamide and wherein the pyrimidine is 2,4-diamino-5-(4-amino-3,5-dimethoxybenzyl)-pyrimidine.

11. A method for combatting bacteria comprising administering to a warmblooded animal requiring such treatment an antibacterially effective amount of a composition comprising 1 to 40 parts of a compound of the formula

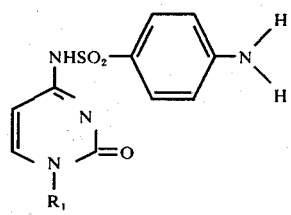

wherein $R_1$ is cyclo-lower alkyl or cyclo-lower alkyl-lower alkyl;

or a pharmaceutically acceptable salt thereof, and 1 part of a compound of the formula

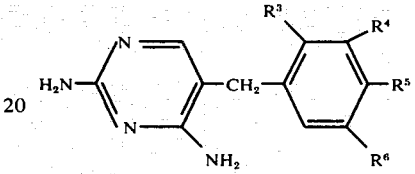

wherein $R^3$ is hydrogen or lower alkyl; $R^4$ is hydrogen or lower alkoxy, $R^5$ is amino, lower alkylamino, di-lower alkylamino or lower alkoxy, and $R^6$ is lower alkoxy, provided that when $R^3$ is lower alkyl, $R^4$ is hydrogen and $R^5$ is lower alkoxy, or a pharmaceutically acceptable acid addition salt thereof.

* * * * *